(12) United States Patent
Harris et al.

(10) Patent No.: US 7,713,488 B2
(45) Date of Patent: May 11, 2010

(54) PRESCENTED AND CUSTOM SCENTED LIGHT FIXTURE ATTACHMENT

(76) Inventors: Neal F. Harris, 527 Avondale Ave., Los Angeles, CA (US) 90049; Daniel Cytrynowicz, 6610 W. 5th St., Los Angeles, CA (US) 90048

( * ) Notice: Subject to any disclaimer, the term of this patent is extended or adjusted under 35 U.S.C. 154(b) by 0 days.

(21) Appl. No.: 12/221,602

(22) Filed: Aug. 5, 2008

(65) Prior Publication Data
US 2009/0068068 A1    Mar. 12, 2009

Related U.S. Application Data

(60) Provisional application No. 60/964,707, filed on Aug. 14, 2007.

(51) Int. Cl.
*A62B 7/08* (2006.01)
(52) U.S. Cl. .................. 422/122; 422/120; 422/125; 422/305; 239/53
(58) Field of Classification Search ........... 422/120, 422/125, 5, 122, 305; 313/315; 392/393; 239/34, 53
See application file for complete search history.

(56) References Cited

U.S. PATENT DOCUMENTS

| | | | |
|---|---|---|---|
| 2,372,371 A | 3/1945 | Eisner | |
| 2,419,357 A | 4/1947 | Krasner, et al | |
| 2,435,756 A | 2/1948 | Schlesinger | |
| 2,557,501 A | 6/1951 | Fusay et al. | |
| 3,084,624 A | 4/1963 | Cheshire | |
| 3,784,102 A | 1/1974 | Stults | |
| 4,009,384 A | 2/1977 | Holland | |
| 4,155,500 A | 5/1979 | Dutcher | |
| 4,167,034 A | 9/1979 | Noguchi | |
| 4,208,012 A | 6/1980 | Dutcher | |
| 4,279,373 A | 7/1981 | Montealegre | |
| 4,280,649 A | 7/1981 | Montealegre | |
| 4,283,011 A | 8/1981 | Spector | |
| 4,346,059 A | 8/1982 | Spector | |
| 4,490,011 A | 12/1984 | Houbregs et al. | |
| 4,493,011 A | 1/1985 | Spector | |
| 4,544,592 A | 10/1985 | Spector | |
| 4,549,250 A | 10/1985 | Spector | |
| 4,579,717 A | 4/1986 | Gyulay | |
| 4,580,581 A | 4/1986 | Reece et al. | |
| 4,647,428 A | 3/1987 | Gyulay | |
| 4,647,433 A | 3/1987 | Spector | |
| 4,809,912 A | 3/1989 | Santini | |
| D301,636 S | 6/1989 | Goutal | |
| D301,760 S | 6/1989 | Goutal | |
| 4,858,831 A | 8/1989 | Spector | |

(Continued)

*Primary Examiner*—Sean E Conley
(74) *Attorney, Agent, or Firm*—Paul M Denk

(57) ABSTRACT

A pre-scented or custom-scented attachment designed to fit onto any existing lamp or lamp shade. The scent attachment allows consumers to choose a scent additive to freshen their home, kitchens, bedroom, bathroom, common-space lobbies, bar, restaurant or any other place where these products are used, as well as to complement the light emitted from the actual light fixture. The attachment can be replaced easily to refresh the space, or change the fragrance for the desired area to be scented. The attachment can be sold with a matching lamp fixture and shade or individually as its own product. It is a shaped attachment, with fragrance embedded therein, being a central hole to fit in the lamp spider, and incorporate grooves to fix it in place.

13 Claims, 2 Drawing Sheets

U.S. PATENT DOCUMENTS

| | | |
|---|---|---|
| 4,892,711 A | 1/1990 | Tendick, Sr. |
| D308,419 S | 6/1990 | Mason |
| 4,965,490 A | 10/1990 | Ratner |
| 5,069,877 A | 12/1991 | Pozzo |
| 5,368,822 A | 11/1994 | McNeil |
| 5,404,286 A | 4/1995 | Boutges |
| D363,537 S | 10/1995 | Moody |
| 5,738,831 A | 4/1998 | Bethel |
| 5,908,231 A | 6/1999 | Huff |
| 6,000,658 A | 12/1999 | McCall, Jr. |
| 6,120,737 A | 9/2000 | Zembrodt |
| 6,152,728 A | 11/2000 | Griffel |
| 6,254,248 B1 | 7/2001 | McAuley et al. |
| 6,328,935 B1 | 12/2001 | Buccellato |
| 6,444,963 B1 | 9/2002 | Donahue |
| 6,478,440 B1 | 11/2002 | Jaworski et al. |
| 6,938,883 B2 | 9/2005 | Adams et al. |
| 6,966,665 B2 | 11/2005 | Limburg et al. |
| 7,008,083 B2 | 3/2006 | Leddusire |
| 7,083,162 B2 | 8/2006 | He et al. |

PRESCENTED AND CUSTOM SCENTED LIGHT FIXTURE ATTACHMENT

CROSS-REFERENCE TO RELATED APPLICATION

This non-provisional patent application claims priority to the provisional patent application having Ser. No. 60/964,707, which was filed on Aug. 14, 2007.

FIELD OF INVENTION

The present invention relates generally to an aroma dispensing device and more particularly to a device for dispensing aroma by lamp or light heat.

BACKGROUND OF THE INVENTION

Over the years, there have been many inventions and attempts made to dispense fragrances that deal with light fixtures, bulbs or from candles. Many of these inventions are elaborate, even motor driven, battery operated, complicated and costly devices. Others may be placed directly onto the light bulb or onto a candle with fragrance oil being directly exposed to the bulb, fixture or open flame. This poses a safety hazard and the consumer potentially may spill or have the fragrance oil come in direct contact with furniture or skin, posing various health, safety and aesthetic risks. Producers of air fresheners have attempted to address this market by incorporating fragrance emitting devices including oils, fans and sprays onto various electrical appliances that plug into typical outlets. This works quite well, but there are several drawbacks.

One prior art aroma dispenser is an aroma dispensing device manufactured by "Delightful Scents" under the name of "light bulb fragrance ring." The device includes a ceramic annulus with a reservoir extending along a top portion thereof. The ceramic annulus is adapted to be received into the reservoir a quantity of an aromatic substance, and adapted to mount directly on a standard incandescent light bulb. The heat given off by the light bulb causes the aromatic substance to vaporize and diffuse into the air. The device permits the user to select a desired aromatic substance for use. However, such devices pose several hazards and limitations. The temperature of a typical incandescent light bulb can reach to at least 5,400° F. at the filament. Since some aromatic substances may be flammable, direct contact of the hot light bulb with the ceramic annulus and the aromatic substance may ignite the latter, thereby creating a dangerous fire hazard. Typical incandescent lamps are further configured to include an electrical light socket which is located below the light bulb. Since liquid aromatic substances are preferably used, such devices may further pose an electrical shock hazard should some of the substance leak down the bulb and into the socket. There is also the danger that the ceramic annulus may break the glass bulb if their respective thermal expansion coefficients are not closely matched.

U.S. Pat. No. 4,858,831 to Spector describes an elaborate air-filled device with jet openings and pressurized chambers that when hand actuated, expel a pulse of fragrance into the atmosphere.

U.S. Pat. No. 4,280,649 to Montealegre, and also U.S. Pat. Nos. 4,279,373, 4,208,012 and 4,155,500, describe a variety of air freshener cartons that are free standing or can be wall mounted and exhibit perforated sleeves, folded flaps or other carton constructions that can be adjusted to allow more or less of a fragrance air freshener material to be released.

U.S. Pat. No. 6,000,658, to McCall, describes a roll spindle and hand ratchet mechanism that activates a music box, a fragrance dispensing apparatus, an audio tape player, and a night light.

The fragrance carrier itself also is the subject matter of many patents. U.S. Pat. No. 4,809,912, to Santini, describes a membrane-gel diffusion device that allows for the controlled release of fragrance gel through a membrane material.

The patent to Spector, U.S. Pat. No. 4,493,011, shows an aromatic disk usable in conjunction with a conventional table lamp that is designed to provide for the emanation of a fragrance.

U.S. Pat. No. 6,120,737, also to Spector, shows a further arrangement for use with a light bulb for emitting a fragrance.

U.S. Pat. No. 7,083,162, to He, provides a device identified as an intermediary device for altering the surrounding environment.

The patent to Pete, et al, U.S. Pat. No. 5,908,231, shows another light bulb fragrance dispenser.

The patent to Huff, U.S. Pat. No. 6,254,248, discloses a controlled fragrance dispenser for light bulb.

The patent to McAuley, et al, U.S. Pat. No. 4,647,428, is another room air freshener, in the form of a porous ceramic ring.

Another patent to Spector, U.S. Pat. No. 4,490,011, shows another type of aroma disk usable in conjunction with a conventional table lamp.

The patent to Jaworski, U.S. Pat. No. 6,478,440, shows another type of air freshener dispenser. A further patent to Gyulay, U.S. Pat. No. 4,579,717, shows another room air freshener.

The patent to Buccellato, U.S. Pat. No. 6,328,935, discloses an aroma dispenser for a candle.

Another patent to Gyulay, U.S. Pat. No. 4,647,428, discloses another room air freshener, in the form of a porous ceramic ring.

The patent to Zembrodt, U.S. Pat. No. 6,120,737, discloses a fragrant light bulb ring.

Other patents relating to this technology include U.S. Pat. No. 1,403,548, upon a lamp vaporizer. U.S. Pat. No. 2,372,371, relating to evaporating disseminator. U.S. Pat. No. 2,419,357, relating to smoke pot cover. U.S. Pat. No. 2,435,756, relating to vaporizing and disseminating device. U.S. Pat. No. 2,557,501, relating to vaporizer. U.S. Pat. No. 3,084,624, relating to die stamping and printing. U.S. Pat. No. 3,784,102, relating to pendant capable of exposing different areas of a volatile tablet. U.S. Pat. No. 4,009,384, relating to lamp scent unit. U.S. Pat. No. 4,167,034, relating to lamp stand for lampshade. U.S. Pat. No. 4,283,011, relating to scented sticker. U.S. Pat. No. 4,346,059, relating to aroma-generating lamp structure. U.S. Pat. No. 4,544,592, relating to aroma-generating capsule. U.S. Pat. No. 4,549,250, relating to night light assembly. U.S. Pat. No. 4,580,581, relating to self deodorizing ash tray. U.S. Pat. No. 4,647,433, relating to long-life aroma-generating capsule. Pat. No. D,301,636, relating to light bulb attachment for supporting scent-releasing pebbles or the like. Pat. No. D,301,760, relating to combined light bulb attachment and scent releasing pebbles therefore. U.S. Pat. No. 4,892,711, relating to fragrance dispensing device. Pat. No. D,308,419, relating to Cover Plate for a ceiling fan. U.S. Pat. No. 4,965,490, relating to Scent-generating lamp using mating parts. U.S. Pat. No. 5,069,877, relating article for diffusing volatile substances, and in particular perfume. U.S. Pat. No. 5,368,822, relating to Vent scent adapter. U.S. Pat. No. 5,404,286, relating to lamp shade adapter. Pat. No. D,363,537, relating to scented decorative ring for lamps. U.S. Pat. No. 5,738,831, relating to bed linen deodorizer. U.S. Pat. No. 6,152,728, relating to Combined drip preventing and fragrance dispensing candle holder. U.S. Pat. No. 6,254,248, relating to Controlled fragrance dispenser for light bulb. U.S. Pat. No. 6,444,963, relating to microwave deodorizer. U.S. Pat. No. 6,938,883, relating to guide for selectively receiving a wick in a dispenser for a volatile liquid. U.S. Pat. No. 6,966,665, relating to flameless candle with air intake chamber and air outflow chamber. U.S. Pat. No. 7,008,083, relating to method and apparatus for leveling a shade.

All of the above prior art patented inventions are more or less cumbersome to assemble and use. Many are very elaborate and costly to manufacture as they incorporate to varying degrees electric motors, valves, pressurized containers, ratchet handles and gears, electronics, wooden cabinets, batteries, moving parts, injection molded components, springs, mounting brackets, gels, complicated membrane packaging or scented oil to be applied to a reservoir by the consumer. The initial cost to purchase and later maintain the refills is relatively high.

SUMMARY OF THE INVENTION

The current invention seeks to overcome the above mentioned issues of cost and safety and offer better, user friendliness and ease of application for home air freshener use.

An attachment is produced through the use of ceramic, absorbent clay, resin, polymer materials or other non flammable fragrance absorbent materials.

A fragrance coating is then applied to the attachment by roller application, spraying, silk screening, and flexography or bath saturation. This coating includes common fragrance oil ingredients as made by companies such as Harris Fragrance, LLC, of Los Angeles, Calif., and IFF Givaudan, and Symrise. These fragrance oils can be modified to achieve the desired end result. One formulation adds polymers to thicken the fragrance and create a thicker coat weight which will also reduce the rate of evaporation. Another formulation may include plasticizing agents that create a scented film-like coating on the surface, again retarding the evaporation process. Other formulations that can retard the evaporation and therefore help achieve a longer lasting product; include dipropylene glycol (DPG), diethylphthylate (DEP) and other common fixatives known by those skilled in the art of fragrance chemistry. On the other hand, additives such as denatured alcohol (39C) may be added to create more lift and speed up the evaporation process, providing a stronger initial fragrance impact, but typically a shorter lasting product.

The above finished product can then be packaged in many conventional ways, including blister packing, pouch packing, or cartoning. These packages can incorporate re-sealable features so that after an attachment is removed, the others remain protected for future use. The primary packaging should provide sufficient odor and fragrance barrier properties so that the product remains moist and fresh for later use. One common and preferred structure includes PVDC coated polyester.

The principal object of this invention is to bring to market and commercialize a low cost, easy and safe method of allowing a customer to add scent to their living space where lamps are commonly utilized, without having to replace existing fixtures or shades. Another object is to provide a customer a wide array of fragrance choices in the after-market purchase of lamps and lamp shades and the joint purchase of theme related lamps and lamp shades.

Still, another principal object of this invention is to allow a customer to spray-apply their own personal body cologne, perfume or aromatherapy oil on an unscented attachment, thereby customizing the product to their personal fragrance preferences.

Other objects and purposes may become more apparent to those skilled in the art upon review of the summary of the invention as provided herein, and upon undertaking a study of the description of its preferred embodiment, in view of the drawings.

DESCRIPTION OF THE PREFERRED EMBODIMENT

Figure 1:
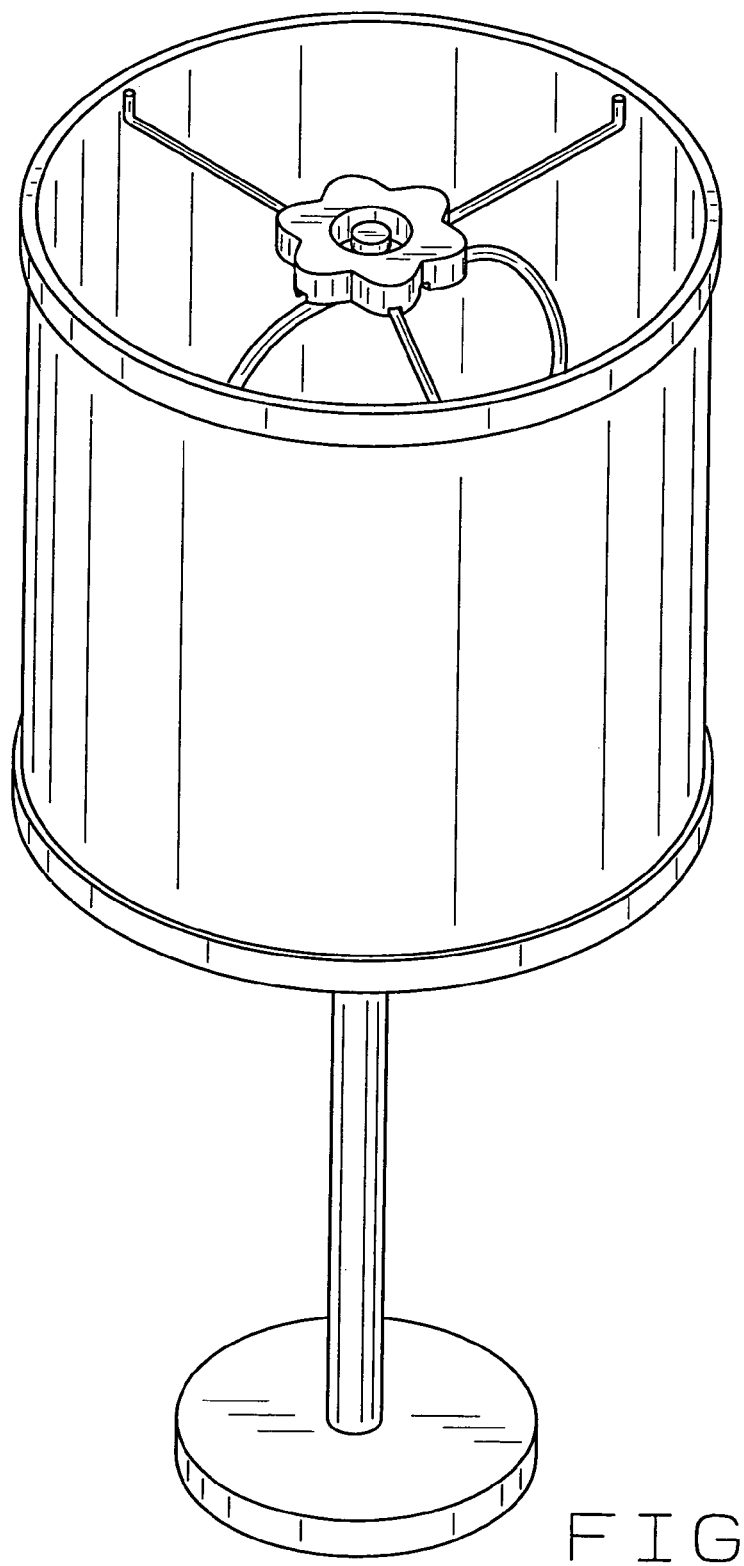
FIG. 1 is a perspective view of a prescented and custom scented attachment, shown located upon a lamp
Figure 2:
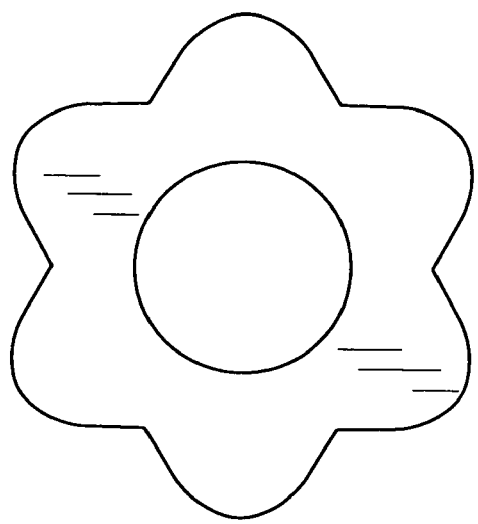
FIG. 2 is a view of the attachment from the top.

Referring initially to FIGS. 1 and 2, an attachment is provided which is capable of absorbing a fragrance. Preferably, the attachment is made from ceramic or clay. The attachment can also be made from porous materials or synthetic carrier materials such as extruded polyethylene or molded polystyrene based materials that will hold fragrance and allow evaporative emittance of the fragrance. Such materials include, for example Tyvek®. Sheeting available from E. I. Dupont de Nemours & Co.; Teslin®, micro porous sheeting available from PPG Industries, Inc. of Pittsburgh, Pa.; Porex®, porous plastic sheeting available from Porex Technologies Corp. of Fairburn, Ga., Celwa® Paper pads, available from John H. Willig d/b/a Celwa Products Co. of New York, N.Y.

The attachment may be round, square, cross shaped or other with grooves in the bottom. The grooves serve to attach the attachment to the spider of a lamp shade. The shown embodiment is petal shaped.

As can be seen in FIG. 2, the attachment 1 may have numerous holes or one large hole as at 2, that allows for air flow and consistent fragrance dispersion throughout the life of the product and allows for the attachment to easily fit onto virtually any lamp shade.

Figure 3:
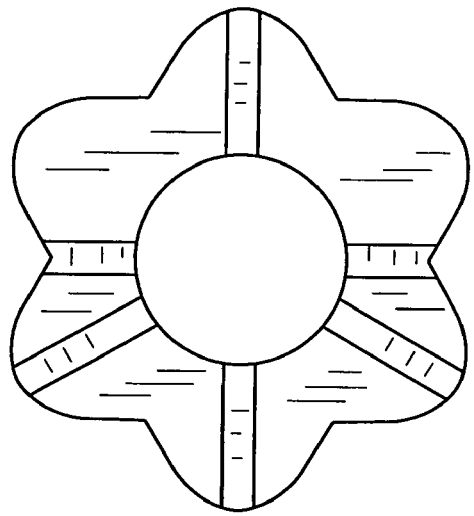
FIG. 3 is a view of the attachment from the bottom.

As can be seen in FIG. 3, the attachment may have numerous grooves 3 that allow for air flow and consistent fragrance dispersion throughout the life of the product while also serving to secure the attachment to the standard lamp shade spider.

Preferably, the attachment is formed in an attractive shape round, oval, square, cross, star shaped or any other appropriate shape with or without decorative graphics, shapes or holes. The graphics shapes or holes can be ornamental or provide functionality for use of the attachments. Such graphics can be printed, impregnated or molded into the shape of the attachment either before or after the shape is formed. One method for printing or impregnating graphics or decorations is by stamping or printing. Also, there may be other holes or apertures, as at 4, provided through the attachment, in order to furnish additional surface area that can be exposed to the heat of the lamp, and allow for evaporation and dissemination of a larger amount of fragrance, during usage of this attachment.

The attachment can be provided as either scented or unscented. If provided as an unscented attachment, the consumer can apply his or her own fragrance to the attachment by either spraying the attachment or dipping the attachment in a desired fragrance (i.e., a perfume, cologne, essential oils, aromatherapy oil, etc.).

If the attachment is pre-scented, the fragrance can be applied either by soaking, dipping, roller or spray application. The fragrance formulation preferably comprises fragrance oil and diluents such as DPG, Benzyl Benzoate, and Carbitol. The preferred fragrance load is approximately 7.0-20 grams per attachment (or about 0.09 gm/in.sup.2). The fragrance applied can include, or be comprised of microencapsulated fragrance oil. This will allow for improved shelf life of the scented application and will provide a refreshing feature to the attachment.

The evaporation of the fragrance from the attachment can be either enhanced or retarded. Evaporation can be retarded by applying a second film of plastisizing agents after the fragrance has been applied to the attachment. Polymers, such as dipropylene glycol (DPG), diethylphthylate (DEP) or similar solvents can also be added to the fragrance formulation to thicken the fragrance coating to achieve a heavier coating weight. This will also retard the rate of evaporation of the fragrance from the attachment. On the other hand, evaporation enhancers, such as denatured alcohol (39C) can be added to the fragrance formulation to increase the rate of evaporation of the fragrance from the attachment.

The attachments are formed as individual pieces. Preferably, they are packaged in a pouch or bag. The preferred packaging is a three-side seal, PVDC coated polyester, foil or Mylar pouch with a heat sealed closure and possibly a hanger hole for peg rack display.

Figure 4:
FIG. 4 is a front view of the attachment.
Figure 5:
FIG. 5 is a back view of the attachment.
Figure 6:
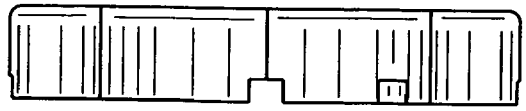
FIG. 6 is a left side view of the attachment.

FIGS. 3 and 4 show how the scented attachment, may be attached to a lamp shade spider, as at 5. As can be seen, the attachment is attached along the wire spider of the lamp shade and held in place by precut or the molded grooves 3 that allow secure attachment to the lamp shade spider. The scented attachment can provide for the emission of a pleasing fragrance.

Variations or modifications to the subject matter of this invention may occur to those skilled in the art upon reviewing the invention as described herein. Such variations, or modifications, to this disclosure, are intended to be encompassed within the scope of the invention. The definition of the invention as set forth in the preferred embodiments, and as depicted in the drawings, are set forth for illustrative purposes only.

What is claimed:

1. A ring-shaped attachment for placement onto the top of a lamp shade and more specifically onto a spider support of said lamp shade the attachment formed from a material which will absorb a fragrance and which is non-flammable, the attachment providing for emission of the fragrance into the ambient air, while exposed to the heat of a lit light bulb of the shade, said attachment in the form of a ring and having at least one hole provided centrally therethrough, and through which a part of the lamp shade spider may locate, said at least one hole providing for fragrance laden air to flow freely therethrough when the lamp is lit; said attachment upon its bottom surface having a series of pre-shaped grooves, extending into the bottom surface of the attachment, said pre-shaped grooves radiating outwardly from the hole arranged centrally of said attachment, said grooves provided for partly accommodating wires of said spider therein during connection of the attachment to the lamp shade, said attachment being impregnated with a fragrance formulation so as to emit a pleasant aroma as the lamp is lit during usage.

2. The attachment of claim 1 in which the attachment may be shaped in a decorative motif.

3. The attachment of claim 1 in which the fragrance formulation includes evaporation enhancers or retardants to control the evaporation rate during usage of the lamp.

4. The attachment of claim 3 in which the evaporation enhancer includes carbitol and denatured alcohol SDA 39c etc.

5. The attachment of claim 3 in which the evaporation retardants include one of dipropylene glycol (DPG) and diethylphthylate (DEP).

6. The attachment of claim 3 in which polymers are added to the fragrance formulation to thicken its coating when applied to the attachment.

7. The attachment of claim 1 in which the fragrance coating is comprised of microencapsulated fragrance oil.

8. The attachment of claim 1 wherein the attachment material is formed from one of extruded polyethylene, molded polystyrene, and polymer-based fragrance materials.

9. The attachment of claim 1 wherein the attachment material is formed from one of ceramic, clay, and related material that can absorb and hold and emit when exposed to heat the evaporative fragrance applied thereto.

10. The attachment of claim 1 wherein a film coating is applied over the fragrance after application of said fragrance to the attachment, said film being formed from material through which the applied fragrance can evaporate, said film as applied regulates the evaporation process of the fragrance from the attachment when heat above the illuminated light" with "said attachment is exposed to heat located above an illuminated light" contained within the lamp.

11. The attachment of claim 10 in which the film comprises plasticizing agents.

12. The attachment of claim 2 wherein the attachment is shaped of one of a ring, cross, square, or oval shape.

13. The attachment of claim 1 wherein said fragrance formulation is impregnated in the attachment at about 0.09 gm/sq. in.

* * * * *